United States Patent
Jackson et al.

(10) Patent No.: US 9,814,874 B2
(45) Date of Patent: Nov. 14, 2017

(54) IMPLANTABLE LEAD ELECTRODE WITH ASYMMETRICALLY DISTRIBUTED CURRENT DENSITY AND METHODS FOR IMPARTING CURRENT DENSITY DIRECTIONALITY IN LEAD ELECTRODES

(75) Inventors: Timothy R. Jackson, Minneapolis, MN (US); Joseph Schroeder, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 750 days.

(21) Appl. No.: 12/946,266

(22) Filed: Nov. 15, 2010

(65) Prior Publication Data

US 2011/0160822 A1 Jun. 30, 2011

Related U.S. Application Data

(60) Provisional application No. 61/291,160, filed on Dec. 30, 2009.

(51) Int. Cl.
*A61N 1/00* (2006.01)
*A61N 1/05* (2006.01)

(52) U.S. Cl.
CPC ...... *A61N 1/056* (2013.01); *A61N 2001/0585* (2013.01)

(58) Field of Classification Search
CPC .............. A61N 1/04; A61N 1/05; A61N 1/056
USPC ................................. 607/119, 122
See application file for complete search history.

(56) References Cited

U.S. PATENT DOCUMENTS

| 4,962,767 A | 10/1990 | Brownlee |
| 4,972,847 A | 11/1990 | Dutcher et al. |
| 4,979,517 A | 12/1990 | Grossman et al. |
| 5,042,463 A | 8/1991 | Lekholm |
| 5,578,067 A | 11/1996 | Ekwall et al. |
| 6,119,044 A | 9/2000 | Kuzma |
| 6,240,322 B1 | 5/2001 | Peterfeso et al. |
| 6,263,249 B1 | 7/2001 | Stewart et al. |
| 6,430,425 B1* | 8/2002 | Bisping .................. 600/374 |
| 6,757,970 B1* | 7/2004 | Kuzma et al. ............. 29/847 |
| 2003/0139794 A1* | 7/2003 | Jenney et al. ............ 607/122 |

(Continued)

FOREIGN PATENT DOCUMENTS

| WO | WO2007001218 A1 | 1/2007 |
| WO | WO2007115198 A2 | 10/2007 |

OTHER PUBLICATIONS

Anderson, Sara E. et al., "Microanatomy of Human Left Ventricular Coronary Veins", The Anatomical Record, vol. 292, pp. 23-28, 2009.

(Continued)

*Primary Examiner* — Mallika D Fairchild

(74) *Attorney, Agent, or Firm* — Faegre Baker Daniels LLP

(57) ABSTRACT

Lead electrodes having an asymmetrically distributed current density and methods for imparting current density directionality in lead electrodes are described. An implantable medical lead includes a lead body having a proximal section that connects to another implantable device and a distal section having a pre-biased shape configured to secure the lead to an inner wall of a body vessel. An electrode coupled to the distal section of the lead body includes a conductor mass having an asymmetrically distributed current density that imparts a directionality to one or more active portions of the electrode.

20 Claims, 6 Drawing Sheets

(56) References Cited

U.S. PATENT DOCUMENTS

| | | | |
|---|---|---|---|
| 2003/0199953 A1* | 10/2003 | Stolz et al. | 607/117 |
| 2005/0049665 A1 | 3/2005 | Brabec et al. | |
| 2005/0060885 A1 | 5/2005 | Johnson et al. | |
| 2005/0222660 A1* | 10/2005 | McAuliffe et al. | 607/122 |
| 2006/0009829 A1 | 1/2006 | Aron et al. | |
| 2006/0121080 A1 | 6/2006 | Lye et al. | |
| 2006/0122681 A1 | 6/2006 | Kroll et al. | |
| 2007/0067008 A1* | 3/2007 | Scheiner et al. | 607/122 |
| 2007/0142890 A1 | 6/2007 | Zarembo et al. | |
| 2008/0057784 A1 | 3/2008 | Zarembo et al. | |
| 2008/0182464 A1 | 7/2008 | Kado et al. | |
| 2009/0248126 A1 | 10/2009 | Nippoldt et al. | |
| 2011/0156306 A1 | 6/2011 | Morris et al. | |
| 2011/0160821 A1 | 6/2011 | Jackson et al. | |
| 2011/0160823 A1 | 6/2011 | De Kock et al. | |

OTHER PUBLICATIONS

United States Statutory Invention Registration No. H1905, to Michael R. S. Hill, published Oct. 3, 2000.
International Search Report and Written Opinion issued in PCT/US2010/058722, dated Mar. 11, 2011.
International Search Report and Written Opinion issued in PCT/US2010/058982, dated Mar. 3, 2011, 12 pages.

* cited by examiner

IMPLANTABLE LEAD ELECTRODE WITH ASYMMETRICALLY DISTRIBUTED CURRENT DENSITY AND METHODS FOR IMPARTING CURRENT DENSITY DIRECTIONALITY IN LEAD ELECTRODES

CROSS-REFERENCE TO RELATED APPLICATION

This application claims priority under 35 U.S.C. §119 to U.S. Provisional Application No. 61/291,160, filed Dec. 30, 2009, entitled "Implantable Lead Electrode With Asymmetrically Distributed Currently Density and Methods For Imparting Current Density Directionality In Lead Electrodes," which is incorporated herein by reference in its entirety for all purposes.

TECHNICAL FIELD

The present invention relates generally to implantable medical devices. More specifically, the present invention relates to lead electrodes having an asymmetrically distributed current density and to methods for imparting current density directionality in lead electrodes.

BACKGROUND

Various types of medical electrical leads for use in cardiac rhythm management (CRM) and neurostimulation applications are known. In CRM applications, for example, such leads are frequently delivered intravascularly to an implantation location on or within a patient's heart, typically under the aid of fluoroscopy. Once implanted, the lead is coupled to a pulse generator or other implantable device for sensing cardiac electrical activity, delivering therapeutic stimuli, and/or for performing some other desired function within the body. Such leads often include a distal, conductor section which contacts the heart tissue, and a proximal, terminal section which is connected to a pulse generator. The distal section of the lead can include a number of ring-shaped electrodes that supply electrical currents to adjacent heart tissue for pacing the heart and/or for sensing heart function. The electrodes are typically attached to a conductor cable or coil within the interior of the lead via a welded, crimped, and/or staked connection joint.

In some lead designs, the distal section of the lead may have a pre-biased shape that is used to secure the lead within the body. In certain lead configurations, for example, the implantable lead can have a helical or S-shaped distal section that serves to secure the lead to the walls of a vein or artery. When implanted within the body, the electrodes may have an inactive portion that does not contact adjacent target tissue, but which affects the current density around the surface of the electrode. Furthermore, in some cases the inactive portion of the electrode can direct current toward an undesired stimulation site such as the phrenic nerve in CRM applications. In some cases, the inactive portion of the electrode not in contact with the target tissue can decrease the amplitude of the current density at the active (i.e., target) region of the electrode, reducing the overall efficiency of the electrode in providing electrical stimulus and/or to sense cardiac electrical activity. For ring-type electrodes having a uniform wall thickness throughout, for example, the electrodes often include one or more inactive portions that are not in contact with the adjacent target body tissue, but which affect the magnitude and directionality of the current density.

SUMMARY

The present invention relates generally to lead electrodes having an asymmetrically distributed current density, and to methods for imparting current density directionality in lead electrodes.

In Example 1, an implantable medical lead in accordance with an illustrative embodiment includes a lead body having a proximal section and a distal section. An electrode coupled to the distal section of the lead body includes a conductor mass having an asymmetrically distributed current density that imparts a directionality to one or more active portions of the electrode.

In Example 2, the medical electrical lead according to Example 1, wherein the electrode includes an active electrode portion and an inactive electrode portion, and wherein the conductor mass on the active electrode portion has a current density greater than the conductor mass of the inactive electrode portion.

In Example 3 the implantable medical lead according to either Example 1 or 2, wherein the electrode comprises an annular-shaped electrode including a first semi-circular section and a second semi-circular section, the first and second semi-circular sections separated from each other via a centerline of the electrode perpendicular to a longitudinal axis of the lead body.

In Example 4, the implantable medical lead according to any of Examples 1-3, wherein a centroid of the electrode is offset from the centerline of the electrode towards the second semi-circular section.

In Example 5, the implantable medical lead according to any of Examples 1-4, wherein a thickness of the second semi-circular section is greater than a thickness of the first semi-circular section.

In Example 6, the implantable medical lead according to any of Examples 1-5, wherein the electrode is coupled to a conductor cable or conductor coil disposed within the lead body, and wherein the connection of the electrode to the conductor cable or conductor coil is at or near the second semi-circular portion.

In Example 7, the implantable medical lead according to Example 6, wherein the electrode is coupled to the conductor cable or conductor coil via a tubular member coupled to an interior portion of the second semi-circular section.

In Example 8, the implantable medical lead according to Example 7, wherein the electrode is coupled to an inwardly extending portion of the second semi-circular section.

In Example 9, the implantable medical lead according to any of Examples 1-8, wherein the electrode comprises an outer conductor body and an inner conductor body coupled to the outer conductor body.

In Example 10, the implantable medical lead according to Example 9, wherein the inner conductor body includes a first section and a second section, the first and second sections separated from each other via a centerline of the electrode perpendicular to a longitudinal axis of the lead body.

In Example 11, the implantable medical lead according to Example 10, wherein a centroid of the inner conductor body is offset from the centerline of the electrode towards the second section of the inner conductor body.

In Example 12, the implantable medical lead according to any of Examples 1-11, wherein the electrode includes a ring-shaped electrode having a windowed section.

In Example 13, the implantable medical lead according to Example 12, wherein the ring-shaped electrode includes at least one insulative layer coupled to the inactive electrode portion.

In Example 14, the implantable medical lead according to either Example 1 or 2, wherein at least one electrode includes a semi-annular electrode having an exterior facing section and an interior facing section, the interior facing section of the electrode including an insulative layer.

In Example 15, the implantable medical lead according to any of Examples 1-14, wherein the at least one electrode includes a plurality of electrodes each having an asymmetrically distributed current density.

In Example 16, the implantable medical lead according to Example 15, wherein the active electrode portions of each electrode are circumferentially offset from each other along the length of the lead body.

In Example 17, an implantable medical lead in accordance with an illustrative embodiment comprises a lead body including a proximal section and a distal section, the distal section of the lead body having a pre-biased shape configured to secure the lead to an inner wall of a body vessel. A plurality of electrodes coupled to and spaced apart along the distal section of the lead body each have an asymmetrically distributed current density configured to impart a directionality to an active portion of the electrode that contacts the inner wall.

In Example 18, a method for imparting current density directionality within an implantable lead electrode comprises determining a target region within the body for implanting an implantable lead, selecting a lead shape suitable for implantation at the target region, and optimizing the current density distribution within an electrode of the implantable lead to impart a directionality at one or more active portions of the electrode configured to contact body tissue at the target region.

In Example 19, the method according to Example 18, wherein optimizing the current density distribution within the electrode includes asymmetrically mass loading the electrode towards the one or more active portions.

In Example 20, the method according to either Example 18 or 19, wherein optimizing the current density distribution within the electrode includes altering the surface geometry of the electrode.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
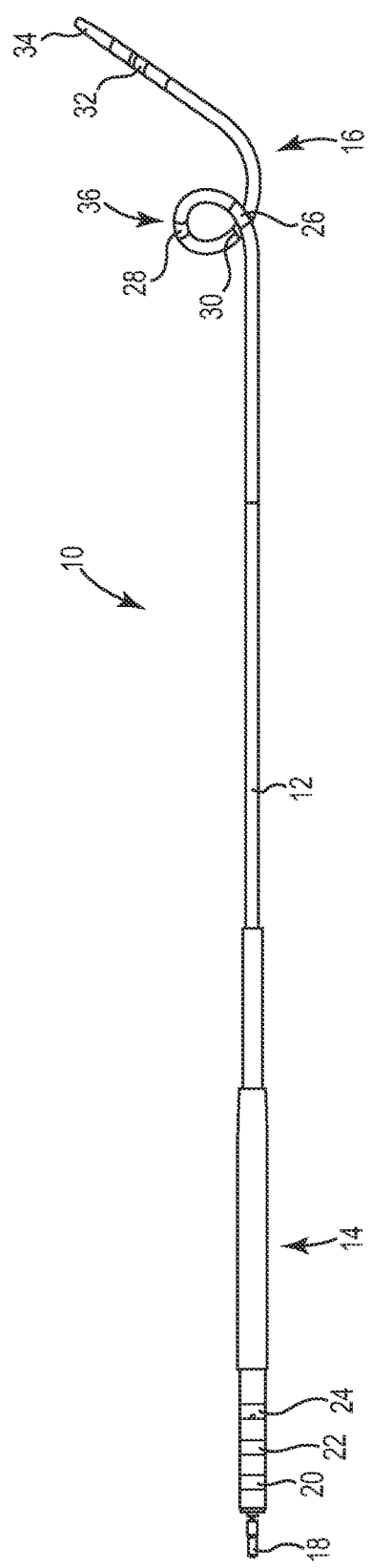
FIG. 1 is a perspective view showing an implantable lead configured for providing electrical stimulus therapy and/or for sensing electrical activity within a patient's body.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view showing an implantable lead 10 configured for providing electrical stimulus therapy and/or for sensing electrical activity within a patient's body. The implantable lead 10, illustratively a quadripolar cardiac lead, includes a lead body 12 having a proximal section 14 and a distal section 16. The proximal section 14 of the implantable lead 10 includes a terminal pin 18 and a number of terminal ring contacts 20,22,24 that connect to a pulse generator such as a pacemaker, implantable cardioverter defibrillator (ICD), cardiac resynchronization therapy (CRT) device, or the like.

The distal section 16 of the implantable lead 10 includes a number of electrodes each coupled to a corresponding cable conductor or coil conductor within the interior of the lead 10. In the embodiment of FIG. 1, for example, the implantable lead 10 includes three electrodes 26,28,30 each electrically connected to a corresponding terminal contact 20,22,24 on the lead 10. Another electrode 32 on the implantable lead 10 is electrically coupled to the terminal pin 18, and is located at a distal tip section 34 of the lead 10 configured to engage the vessel wall. During operation, a pulse generator supplies electrical pulses to the electrodes 26,28,30,32 for pacing the heart and/or for sensing cardiac electrical activity.

In certain embodiments, the distal section 16 has a pre-biased shape that engages the inner diameter of a vessel wall to secure the lead 10 within a blood vessel and/or to promote electrode contact with target tissue. As shown in FIG. 1, for example, the distal section 16 includes a pre-biased helical section 36 that can be used to secure the lead 10 to the inner wall of a coronary vein, pulmonary artery, or other such vessel. In other applications such as neurostimulation applications, the distal section 16 can be positioned outside of a vessel such as the carotid sheath, or can be positioned in other body lumens. Other configurations of the distal section 16 are also possible. In one alternative embodiment, for example, the distal section 16 of the implantable lead 10 can include an S-shaped or J-shaped configuration for insertion within a blood vessel or within a chamber of the heart. The shape imparted to the distal section 36 will typically vary based on the anatomy at the implantation location and the delivery mechanism. As discussed further below, the orientation of the electrodes 26,28,30,32 can also vary depending on the particular shape imparted to the implantable lead 10.

Figure 2:
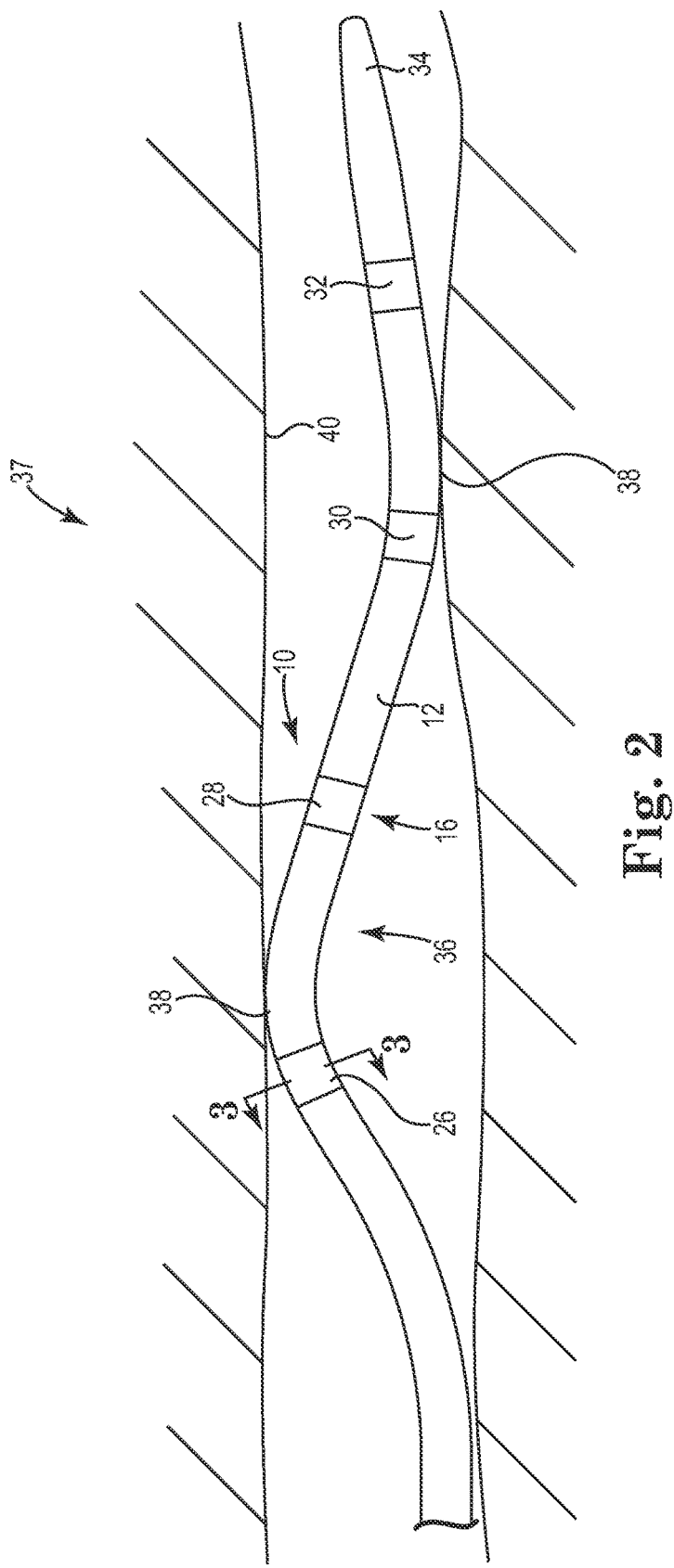
FIG. 2 is a schematic view showing the implantable lead of FIG. 1 inserted at a target region within a blood vessel.

FIG. 2 is a schematic view showing the implantable lead 10 of FIG. 1 inserted at a target region within a blood vessel such as a coronary vein 37. As further shown in FIG. 2, when inserted into the vein 37, an outwardly-facing portion 38 of the helical section 36 is configured to engage the inner wall 40 of the vein 37, which in addition to the distal tip section 34, frictionally secures the lead 10 in place within the vein 37. In some embodiments, the inwardly-directed force from the inner wall 40 of the vein 37 opposes the outwardly-directed force from the helical section 36, which further serves to frictionally secure the implantable lead 10 within the vein 37.

As further shown in FIG. 2, and in some embodiments, the electrodes 26,28,30,32 each comprise ring-type electrodes spaced apart from each other along the length of the lead body 12 for pacing and/or sensing at various locations along the length of the vein 37. The electrodes 26,28,30,32 are each fabricated from an electrically conductive material such as platinum, palladium, titanium, gold, or MP35N. Due to the helical shape of the implantable lead 10 at section 36, only a portion of each of the electrodes 26,28,30,32 contacts the inner wall 40 of the vein 37. As further shown across line 3-3 in FIG. 3, for example, only an active, outer facing portion 42 of the electrode 26 contacts the inner wall 40 of the vein 37. An inwardly facing, inactive portion 44 of the electrode 26 oriented towards the interior of the vein 37, in turn, does not contact the inner wall 40.

On implantable leads having a pre-biased shape, the location(s) where the lead contacts the vessel wall can often be reliably predicted. In such case, and in some embodiments, the orientation of the active, outer facing portion 42 and inactive, inwardly facing portion 44 of the electrodes 26,28,30,32 may vary depending on the shape of the lead and the surrounding anatomy. In a helical-shaped configuration such as that shown in FIG. 2, for example, the active electrode portion of each of the three electrodes 26,28,30 on the helical section 36 can be offset circumferentially at different angles from each other based on the path of the helix. In one embodiment, for example, each of the electrodes 26,28,30 can each be circumferentially offset from each other at an angle of between 30° to 60° around the lead body 12. Other configurations are also possible.

The current density within each of the electrodes 26,28,30,32 can be defined generally as a vector representing the electrical current per unit area of cross section. The directional aspect of the current density vector is related to the location of the internal conductor mass within the electrode 26,28,30,32. Factors that can affect the magnitude and direction of the current density within the electrode can include the distribution of conductor mass within the electrode, the geometry of the electrode, the surface characteristics of the electrode, the material of the electrode, as well as other factors. During pacing and/or sensing, the current density within the electrode 26,28,30,32 affects the amount of current that is delivered to the adjacent body tissue.

Figure 3:
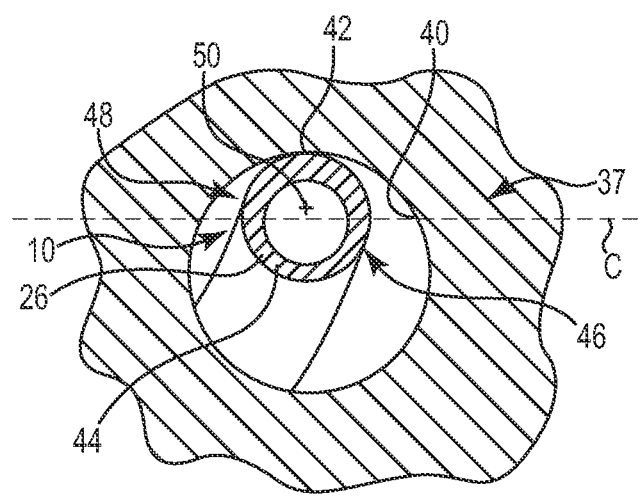
FIG. 3 is a transverse cross-sectional view of the electrode across line 3-3 in FIG. 2.

As can be further understood with respect to FIG. 3, the electrode 26 comprises an annular-shaped conductor body 44 having a first semi-circular section 46 and a second semi-circular section 48. The first and second sections 46,48 are separated from each other via an imaginary centerline C, which extends across the width of the electrode 26 perpendicular to its longitudinal axis. In the embodiment shown, the thickness of the second section 48 is greater than the thickness of the first section 46 such that a greater amount of conductor mass is located towards the outer facing portion 42 adjacent to the vessel wall 40. Due to the increased conductor mass in the second section 48, the centroid 50 of the electrode 26 is directed more towards the outer facing portion 42 and away from the inner facing portion 44. In use, the greater amount of conductor mass towards the outer facing portion 42 increases the current density at this location, imparting a directionality towards the active portion of the electrode 26 that contacts the myocardial tissue on the inner wall 40 of the vein 37. This directionality towards the myocardium and away from other regions in the vein 37 increases the ability of the electrode 26 to pace and sense while also reducing undesired stimulation of other regions of the body.

Figure 4:
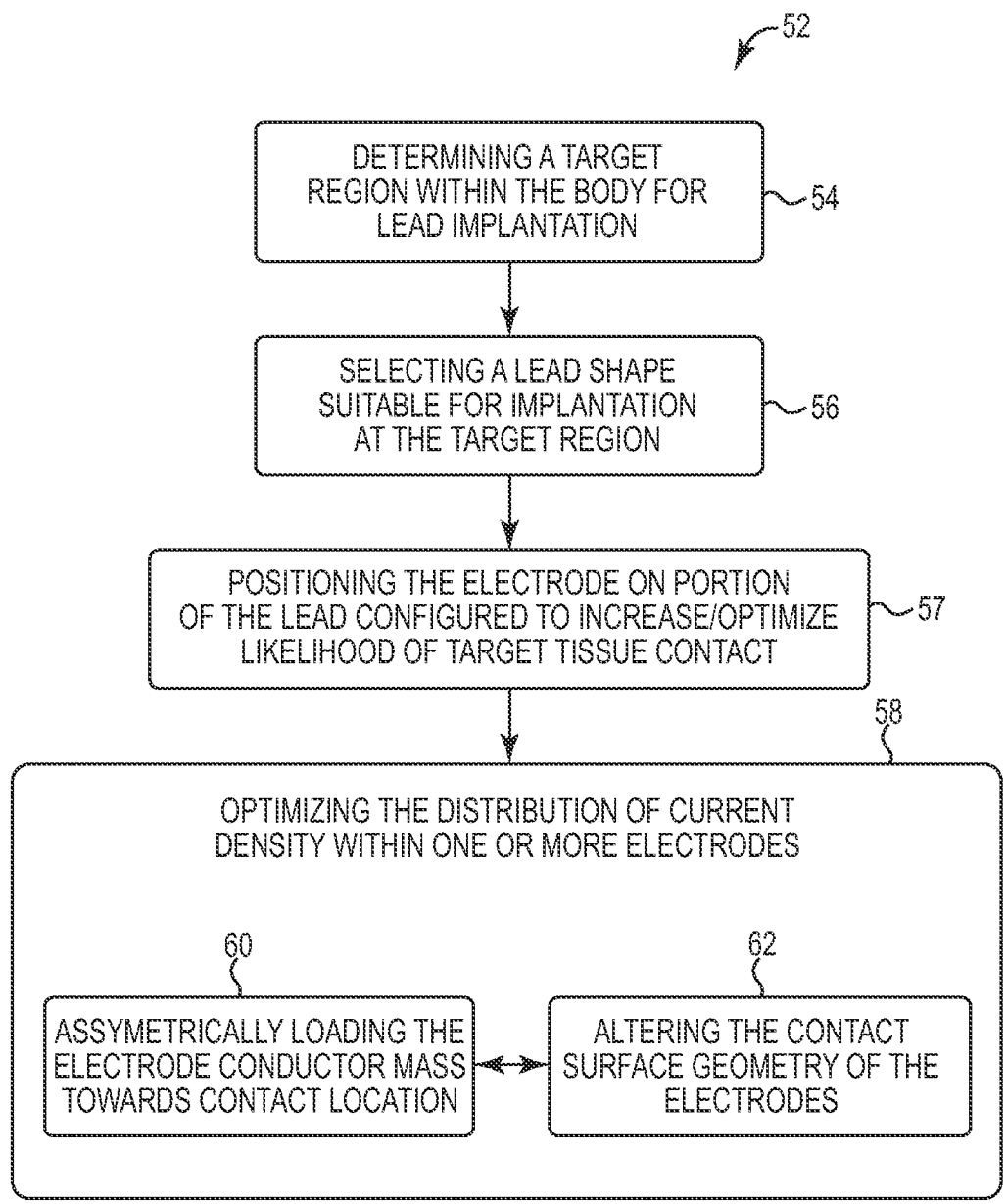
FIG. 4 is a flow diagram showing an illustrative method of imparting current density directionality to a lead electrode.

FIG. 4 is a flow diagram showing an illustrative method 52 for imparting current density directionality to a lead electrode. The method 52 may comprise, for example, several illustrative steps that can be used as part of a design process or selection process to improve, and in some cases optimize, pacing and/or sensing by manipulating the current density directionality in one or more of the electrodes 26,28,30,32 of an implantable lead 10. The method 52 can be performed, for example, by modifying the mass distribution of conductor mass within one or multiple electrodes 26,28,30,32 in the embodiment of FIG. 1, and/or by modifying the surface geometry of one or more of the electrodes 26,28,30,32.

The method 52 may begin by determining a target region within the body for implanting an implantable lead (block 54), and then selecting a lead shape suitable for implantation at the target region (block 56). In the example of FIG. 2 in which the target region is a coronary vein 37, the implantable lead 10 selected can include a helical section 36 sized and shaped to frictionally engage the inner wall 40 of the vein 37. If, in other embodiments, the implantable lead is configured for insertion within a chamber of the heart (e.g., the right ventricle) or at another target region within the vasculature (e.g., within a pulmonary artery), the type of implantable lead selected may vary from that shown in FIG. 1. In one alternative embodiment, for example, the implantable lead selected may have an S-shaped or J-shaped distal section. In some embodiments, the method 52 further includes positioning the electrode on a portion of the lead configured to increase, and in some cases optimize, the likelihood of target tissue contact (block 57).

At block 58, the method 52 further includes the step of optimizing the current density distribution within an electrode to impart a directionality at one or more active portions of the electrode that contact adjacent body tissue when implanted within the body. Such optimization can be performed, for example, by asymmetrically distributing the conductor mass of the electrode more towards the location where the electrode is to contact the body tissue, as indicated generally at block 60. The asymmetric distribution of the conductor mass towards the contact location can be accomplished, for example, by increasing the thickness of the electrode at the active location of the electrode expected to contact adjacent body tissue (e.g., myocardium) while at the same time reducing the thickness of the electrode and/or removing one or more portions of the electrode at the location where the electrode is not expected to contact the tissue (e.g., adjacent to the pericardium or phrenic nerve). Increasing the conductor mass at or near the active portion(s) of the electrode can also be accomplished by the use of different conductor materials, or by the materials used for coupling the electrode to the conductor cable or coil.

In some embodiments, asymmetric mass loading of the conductor mass can be accomplished by coupling the electrode to its associated conductor cable or conductor coil at or near the location where the electrode contacts adjacent body tissue to increase the conductor mass at this location. For example, the location of the weldment or staking can be made at or near the active portion of the electrode in order to increase the conductor mass at this location. In one embodiment, for instance, a staking post used to electrically connect the electrode to a cable conductor or coil conductor can be coupled to the electrode at or near the area of desired stimulation (e.g., the myocardium). This addition of an asymmetric mass element (e.g., staking post) to the electrode results in an area of maximized current density on the surface of the electrode that is tangent to the center of the added mass element. A number of other asymmetrically mass-loaded electrodes in accordance with several other embodiments are further described with respect to FIGS. 5-10.

In some embodiments, and as further shown at block 62, optimizing the current density distribution within an electrode to impart a directionality towards the active location of the electrode can be performed by altering the surface geometry of the electrode. In certain embodiments, for example, the surface geometry of the electrode can be adjusted by altering the size and shape of the electrode and/or by selectively removing portions of the electrode. A number of electrodes having a modified surface geometry in accordance with several embodiments are further described with respect to FIGS. 11-12.

In some embodiments, the process of asymmetrically distributing the conductor mass (block 60) and altering the surface geometry of the electrode (block 62) can both be performed as part of the step (block 58) of optimizing the current density distribution within an electrode. Alternatively, and in other embodiments, the optimizing step 58 includes either asymmetrically distributing the conductor mass (block 60) or altering the surface geometry (block 62). Other techniques for optimizing the current density distribution within an electrode are also possible. Several examples of an implantable lead having a modified electrode surface for imparting current density directionality in a lead electrode is disclosed, for example, in U.S. Pat. No. 8,463,398, entitled "Electrode Surface Modification For Imparting Current Density Directionality in Lead Electrodes," the contents of which is incorporated herein by reference in its entirety.

Figure 5:
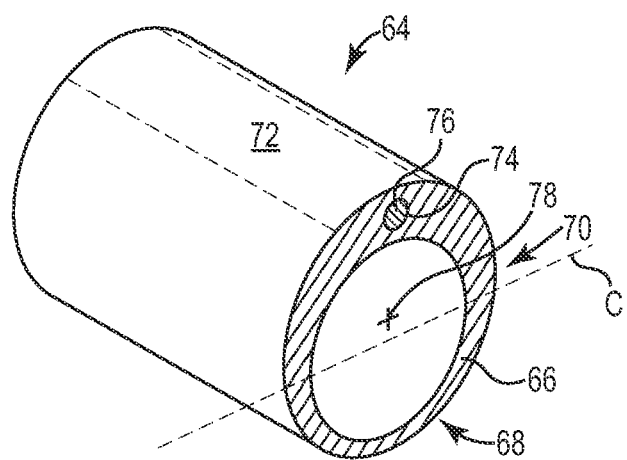
FIG. 5 is a perspective view showing an asymmetrically mass-loaded electrode in accordance with an illustrative embodiment.
Figure 6:
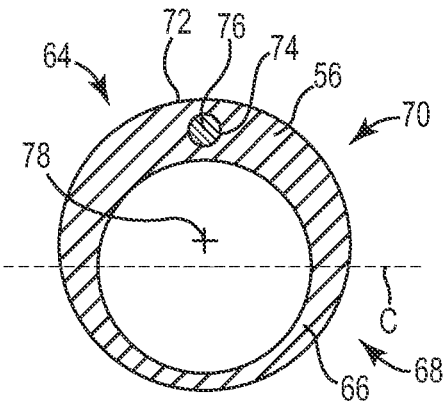
FIG. 6 is a transverse cross-sectional view of the electrode of FIG. 5.

FIGS. 5-6 are several views showing another asymmetrically mass-loaded electrode 64 in accordance with an illustrative embodiment. As shown in FIGS. 5-6, the electrode 64 comprises an annular-shaped conductor body 66 having a first semi-circular section 68 and a second semi-circular section 70. The first and second sections 68,70 are separated from each other via an imaginary centerline C, which extends across the width of the electrode 64 perpendicular to its longitudinal axis.

In the embodiment shown, the thickness of the second section 70 is greater than the thickness of the first section 68 such that a greater amount of conductor mass is located towards an active, exterior contact surface 72 adjacent to the second section 70. A stake or weld hole 74 located at or near the exterior contact surface 72, in turn, is configured to receive a stake pin 76 for connecting the electrode 64 to a conductor cable within the implantable lead. Due to the increased conductor mass in the second section 70 of the electrode 64, and due to the additional mass at the location where the stake pin 76 is received within the stake or weld hole 74, the centroid 78 of the electrode 64 is directed more towards the exterior contact surface 72 which, during implantation, contacts the adjacent body tissue. This asymmetric mass loading imparts a directionality to the electrode 64 that increases the current density at or near the location where the electrode 64 contacts the adjacent body tissue. During pacing and/or sensing, this directionality towards the active, exterior contact surface 72 increases current flow into the body tissue while also reducing undesired stimulation of other areas within the vessel.

Figure 7:
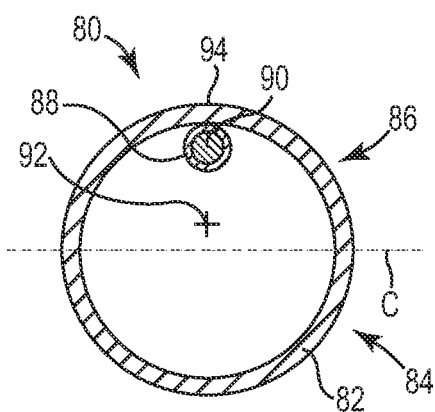
FIG. 7 is a transverse cross-sectional view showing an asymmetrically mass loaded electrode in accordance with another illustrative embodiment.

FIG. 7 is a transverse cross-sectional view showing an asymmetrically mass loaded electrode 80 in accordance with another illustrative embodiment. As shown in FIG. 7, the electrode 80 comprises an annular-shaped conductor body 82 having a first semi-circular section 84 and a second semi-circular section 86. The first and second sections 84,86 are separated from each other via an imaginary centerline C, which extends across the width of the electrode 80 perpendicular to its longitudinal axis. In the embodiment shown, the thickness of the conductor body 82 is uniform at each section 84,86. A tubular member 88 coupled to an interior portion of the second section 86 is configured to receive a stake pin 90 for connecting the electrode 80 to a conductor cable or conductor coil within the implantable lead. Due to the increased conductor mass from the presence of the tubular member 88 and stake pin 90 at the second section 86, the centroid 92 is directed more towards the exterior contact surface 94 of the electrode 80 that contacts the adjacent body tissue.

Figure 8:
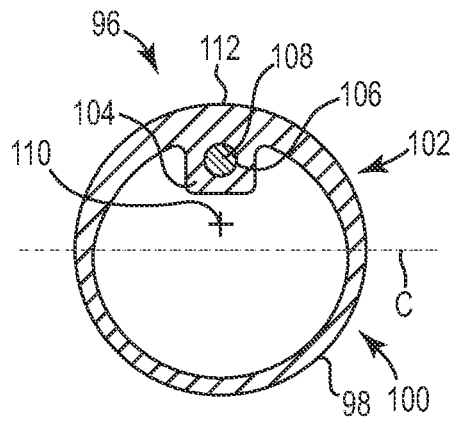
FIG. 8 is a transverse cross-sectional view showing an asymmetrically mass loaded electrode in accordance with another illustrative embodiment.

FIG. 8 is a transverse cross-sectional view showing an asymmetrically mass loaded electrode 96 in accordance with another illustrative embodiment. As shown in FIG. 8, the electrode 96 comprises an annular-shaped conductor body 98 having a first semi-circular section 100 and a second semi-circular section 102. The first and second sections 100,102 are separated from each other via an imaginary centerline C, which extends across the width of the electrode 96 perpendicular to its longitudinal axis. In the embodiment shown, the thickness of the second section 102 is greater than the first section 100. An inwardly extending portion 104 on the second section 102 includes a stake or weld hole 106 that receives a stake pin 108 for connecting the electrode 96 to a conductor cable or conductor coil within the implantable lead. Due to the increased conductor mass in the second section 102, and due to the additional conductor mass at the location where the stake pin 108 is received within the stake or weld hole 106, the centroid 110 for the electrode 96 is directed more towards the exterior contact surface 112 that contacts the adjacent body tissue.

Figure 9:
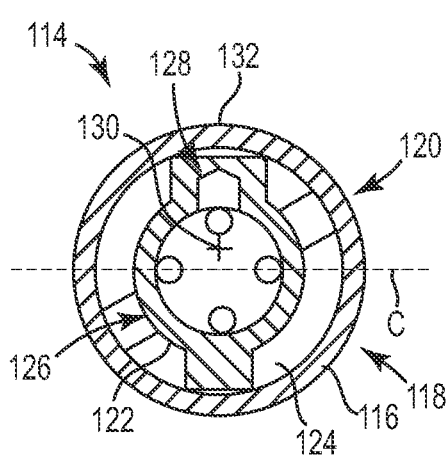
FIG. 9 is a transverse cross-sectional view showing an asymmetrically mass loaded electrode in accordance with another illustrative embodiment.

FIG. 9 is a transverse cross-sectional view showing an asymmetrically mass loaded electrode 114 in accordance with another illustrative embodiment. As shown in FIG. 9, the electrode 114 comprises a first, outer conductor body 116 having a first semi-circular section 118 and a second semi-circular section 120. The first and second sections 118,120 are separated from each other via an imaginary centerline C, which extends across the width of the electrode 114 perpendicular to its longitudinal axis. In the embodiment shown, the electrode 114 further includes a second, inner conductor body 122 disposed within an interior lumen 124 of the first conductor body 116. In contrast to the first conductor body 116, the second conductor body 122 is asymmetric in a plane perpendicular to the centerline axis C, and includes a first portion 126 having a lower conductor mass than a second portion 128. Due to the increased conductor mass in the second section 128, the centroid 130 for the electrode 114 is directed more towards the external contact surface 132 that contacts the adjacent body tissue.

Figure 10:
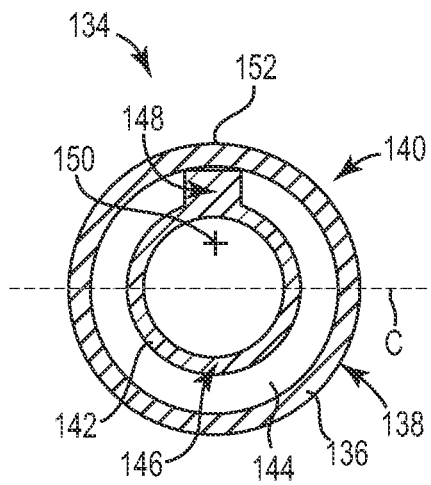
FIG. 10 is a transverse cross-sectional view showing an asymmetrically mass loaded electrode in accordance with another illustrative embodiment.

FIG. 10 is a transverse cross-sectional view showing an asymmetrically mass loaded electrode 134 in accordance with another illustrative embodiment. As shown in FIG. 10, the electrode 134 comprises a first, outer conductor body 136 having a first semi-circular section 138 and a second semi-circular section 140. The first and second sections 138,140 are separated from each other via an imaginary centerline C, which extends across the width of the electrode 134 perpendicular to its longitudinal axis. In the embodiment shown, the electrode 134 further includes a second, inner conductor body 142 disposed within an interior lumen 144 of the first conductor body 136. In contrast to the first conductor body 136, the second conductor body 142 is asymmetric in a plane perpendicular to the centerline axis C, and includes a first portion 146 having a lower conductor mass than a second portion 148. Due to the increased conductor mass in the section portion 148, the centroid 150 for the electrode 134 is directed more towards the external contact surface 152 that contacts the adjacent body tissue.

Figure 11:
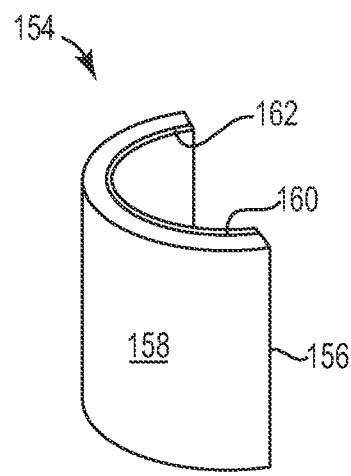
FIG. 11 is a perspective view showing an electrode having an altered surface geometry in accordance with an illustrative embodiment.

FIG. 11 is a perspective view showing an electrode 154 having an altered surface geometry in accordance with an illustrative embodiment. As shown in FIG. 11, the electrode 154 comprises a semi-annular conductor body 156 having an exterior surface 158 and an interior surface 160. The exterior surface 158 of the electrode 154 is exposed on the exterior of the lead, and is configured to contact the inner wall of a vein or artery. The interior surface 160 of the electrode 154, in turn, faces the interior of the lead, and does not contact the inner wall.

In some embodiments, the interior surface 160 of the electrode 154 further includes a layer of insulative material 162 (e.g., PEEK, TECOTHANE, silicone), which in addition to insulating the electrode 154, also affects the current density directionality within the electrode 154. Other portions of the lead can also include an insulator to further prevent current flow in other, undesired directions. In use, the insulative layer 162 on the electrode 154 and/or the insulation within the interior of the lead serves to increase the current density in the adjacent body tissue as well as decrease the current density in other directions which may lead to undesired stimulation of other anatomy (e.g., the pericardium or phrenic nerve). In some embodiments, a drug plug/collar may also be applied to the portions of the electrode 154, which further serves to insulate the electrode 154. Insulation can also be provided in other electrode embodiments to increase the current density directionality.

In certain embodiments, the electrode 154 may comprise part of an implantable lead having a pre-shaped distal section. With respect to the helically biased lead 10 shown in FIG. 1, for example, the semi-annular electrode 154 may be used in lieu of the ring-shaped electrodes 26,28,30,32 for providing pacing therapy and/or for sensing cardiac electrical activity. The semi-annular electrode 154 can be located at select locations along the length of the implantable lead 10 such that the exterior surface 158 of the electrode 154 contacts the vessel wall tangentially across its face.

In some cases, the alignment of the electrodes 154 relative to the vessel wall can increase current density. As the alignment of the electrode 154 increases beyond about 100°, however, the current density within the electrode 154 at the area of contact falls off precipitously. During deployment of the implantable lead 10 within the body, and in some embodiments, the electrodes 154 can therefore be oriented such that the electrodes 154 are aligned at an angle of between about 0° to 100° relative to the axis of stimulation. In some embodiments, for example, the implantable lead 10 can be manipulated within the vessel such that the electrodes 154 are aligned between about 45° to 90°relative to the axis of stimulation. In some embodiments, this off-axis alignment of the electrode 154 relative to the axis of stimulation increases the current density in a direction towards the body tissue as compared to the same electrode 154 aligned with the stimulation axis.

Figure 12:
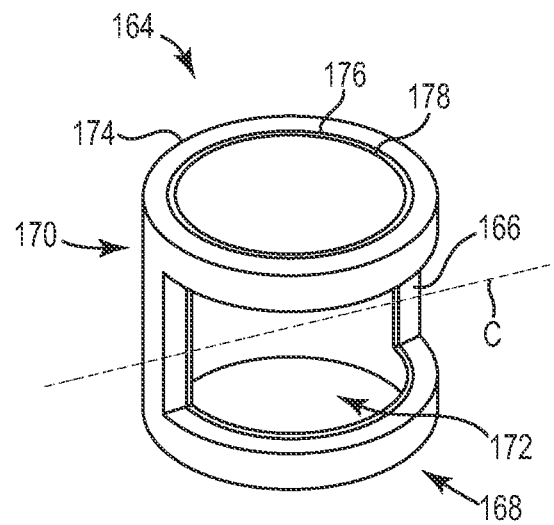
FIG. 12 is a perspective view showing an electrode having an altered surface geometry in accordance with another illustrative embodiment.

FIG. 12 is a perspective view showing an electrode 164 having an altered surface geometry in accordance with another illustrative embodiment. As shown in FIG. 12, the electrode 164 comprises an annular-shaped conductor body 166 having a first semi-annular section 168 and a second semi-annular section 170. The first and second sections 166,168 are separated from each other via an imaginary centerline C, which extends across the width of the electrode 164 perpendicular to its longitudinal axis.

In the embodiment shown, a portion of the body 166 is removed, forming a windowed section 172 in the first section 168. The removal of the body 166 at this location decreases the conductor mass in the first section 168 as compared to the second section 170, imparting a directionality to the electrode 164 that increases the current density at or near an external contact surface 174 on the second section 170. When implemented as part of an implantable lead 10 having a pre-shaped distal section, the lead 10 can be manipulated so that the exterior contact surface 174 of the electrode 164 contacts the adjacent body tissue to be stimulated. In some embodiments, the interior surface 176 of the electrode 164 further includes a layer of insulative material 178, which in addition to insulating the electrode 164, also affects the current density directionality within the electrode 164. In some embodiments, a drug plug/collar may also be applied to portions of the electrode 164, which further serves to insulate the electrode 164.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. An implantable medical lead, comprising:
   a lead body including a proximal section and a distal section, the distal section having a pre-biased shape configured to engage a wall of a blood vessel to secure the lead within the blood vessel; and
   at least one electrode coupled to the distal section of the lead body, each electrode of the at least one electrode comprising an active portion and an inactive portion, the active portion having a first thickness perpendicular to a longitudinal axis of electrode at a cross section of the electrode, each of the active portion and the inactive portion having a respective conductive electrode surface exposed on an exterior of the implantable medical lead, the inactive portion having a second thickness perpendicular to the longitudinal axis of electrode at the cross section, the active portion having an exterior contact surface and the inactive portion having an exterior surface, the active portion and the inactive portion oriented along the pre-biased shape such that the exterior contact surface of the active portion is outward facing and configured to engage the wall of the blood vessel and the exterior surface of the inactive portion is inward facing to not engage the wall of the blood vessel;

wherein each electrode of the at least one electrode has an asymmetrical conductor mass having a greater mass at the active portion as compared to the inactive portion due to the first thickness being greater than the second thickness, the asymmetrical conductor mass imparting an asymmetrically distributed current density having greater current density at the active portion than at the inactive portion.

2. The implantable medical lead of claim 1, wherein the electrode is an annular-shaped electrode.

3. The implantable medical lead of claim 2, wherein the electrode comprises a first semi-circular section forming the inactive portion and a second semi-circular section forming the active portion, the first and second semi-circular sections separated from each other via a centerline of the electrode perpendicular to a longitudinal axis of the lead body.

4. The implantable medical lead of claim 3, wherein a centroid of the electrode is offset from the centerline of the electrode towards the second semi-circular section.

5. The implantable medical lead of claim 4, further comprising a conductor cable or conductor coil disposed within the lead body and coupled to the electrode, and wherein a connection of the electrode to the conductor cable or conductor coil is at or near the second semi-circular portion relative to the first semi-circular portion.

6. The implantable medical lead of claim 5, further comprising a tubular member coupled to an interior portion of the second semi-circular section, wherein the electrode is coupled to the conductor cable or conductor coil via the tubular member.

7. The implantable medical lead of claim 5, further comprising an inwardly extending portion of the second semi-circular section, wherein the electrode is coupled to the inwardly extending portion.

8. The implantable medical lead of claim 2, wherein the electrode comprises:
an outer conductor body; and
an inner conductor body coupled to the outer conductor body.

9. The implantable medical lead of claim 8, wherein the inner conductor body includes a first section and a second section, the first and second sections separated from each other via a centerline of the electrode perpendicular to a longitudinal axis of the lead body.

10. The implantable medical lead of claim 9, wherein a centroid of the inner conductor body is offset from the centerline of the electrode towards the second section of the inner conductor body.

11. The implantable medical lead of claim 2, wherein the electrode includes a windowed section.

12. The implantable medical lead of claim 11, wherein the electrode includes at least one insulative layer coupled to the inactive electrode portion.

13. The implantable medical lead of claim 2, wherein the at least one electrode includes an exterior facing section and an interior facing section, the interior facing section of the electrode including an insulative layer.

14. The implantable medical lead of claim 2, wherein the at least one electrode includes a plurality of electrodes each having the asymmetrically distributed current density.

15. The implantable medical lead of claim 14, wherein the active electrode portions of each electrode are circumferentially offset from each other along a length of the lead body.

16. The implantable medical lead of claim 1, wherein an orientation of the active portion and the inactive portion along the pre-biased shape and the asymmetrical conductor mass direct electrical current towards myocardium and away from other tissue regions to reduce undesired stimulation of the other tissue regions.

17. The implantable medical lead of claim 1, wherein the pre-biased shape is a helical shape.

18. The implantable medical lead of claim 1, wherein each electrode of the at least one electrode is a ring electrode having a circular outer circumference and a circular lumen, the electrode having the asymmetrical conductor mass due at least in part to a center of a cross section of the circular outer circumference being offset from a center of a cross section of the circular lumen.

19. An implantable medical lead, comprising:
a lead body including a proximal section and a distal section, the distal section having a pre-biased shape configured to engage tissue; and
a ring-shaped electrode coupled to the distal section of the lead body, the electrode having a circular outer circumference having a first center at a cross section of the electrode perpendicular to a longitudinal axis of electrode and a circular lumen having a second center at the cross section, the first center offset from the second center, the electrode comprising an active portion and an inactive portion, the active portion having an exterior contact surface and the inactive portion having an exterior surface, the active portion and the inactive portion oriented along the pre-biased shape such that the exterior contact surface of the active portion is outward facing and configured to engage the tissue and the exterior surface of the inactive portion is inward facing to not engage the tissue,
wherein the electrode has an asymmetrical conductor mass having a greater mass at the active portion as compared to the inactive portion due to the first center being offset from the second center, the asymmetrical conductor mass imparting an asymmetrically distributed current density having greater current density at the active portion than at the inactive portion.

20. An implantable medical lead, comprising:
a lead body including a proximal section and a distal section, the distal section having a pre-biased shape configured to engage tissue;
a ring-shaped electrode coupled to the distal section of the lead body, the electrode comprising an active portion and an inactive portion, the active portion having an exterior conductive contact surface and the inactive portion having an exterior conductive surface, each of the exterior conductive contact surface of the active portion and the exterior conductive surface of the inactive portion exposed on an exterior of the implantable medical lead, the active portion and the inactive portion oriented along the pre-biased shape such that the exterior contact surface of the active portion is outward facing and configured to engage the tissue and the exterior surface of the inactive portion is inward facing to not engage the tissue; and
a conductor cable or conductor coil extending within the lead body and coupled to the electrode at a location on the active portion, the active portion having an additional mass at the location to receive the conductor cable or the conductor coil,
wherein the electrode has an asymmetrical conductor mass having a greater mass at the active portion as compared to the inactive portion due to the active portion having the additional mass, the asymmetrical conductor mass imparting an asymmetrically distributed current density having greater current density at the active portion than at the inactive portion.

* * * * *